United States Patent [19]

Meier et al.

[11] Patent Number: 5,281,740
[45] Date of Patent: Jan. 25, 1994

[54] PROCESS FOR THE PREPARATION OF 3′-AMINOPROPYL 2-SULFATOETHYL SULFONE

[75] Inventors: Michael Meier; Heinrich Angenendt, both of Frankfurt am Main, Fed. Rep. of Germany

[73] Assignee: Hoechst Aktiengesellschaft, Frankfurt am Main, Fed. Rep. of Germany

[21] Appl. No.: 923,955

[22] PCT Filed: Feb. 27, 1991

[86] PCT No.: PCT/EP91/00359

§ 371 Date: Sep. 4, 1992

§ 102(e) Date: Sep. 4, 1992

[87] PCT Pub. No.: WO91/13866

PCT Pub. Date: Sep. 19, 1991

[30] Foreign Application Priority Data

Mar. 7, 1990 [DE] Fed. Rep. of Germany ....... 4007049

[51] Int. Cl.⁵ .......................................... C07C 305/04
[52] U.S. Cl. ..................................................... 558/29
[58] Field of Search ................... 558/29; 564/500, 501

[56] References Cited

U.S. PATENT DOCUMENTS

2,824,887  2/1958  Klopping .

FOREIGN PATENT DOCUMENTS

0141776  5/1985  European Pat. Off. .
2040620  2/1972  Fed. Rep. of Germany .

*Primary Examiner*—Nicky Chan

[57] ABSTRACT

In a method for preparing 3′-aminopropyl-2-sulphatoethylsulphone in a one-pot process, allyl amine is reacted with mercaptoethanol in dilute sulphuric acid at temperatures of approximately 50° C. up to the boiling point in the presence of a radical starter. The resultant reaction mixture is oxidized with hydrogen peroxide, in the presence of catalytic quantities of a compound of a transition metal of the periodic system of the elements as an oxidation catalyst, at temperatures of approximately 70 to 100°C. and evaporated to dryness after addition of sufficient sulphuric acid to bring the total sulphuric acid content of the mixture to at least 1 mol, referred to the quantity of allyl amine used.

12 Claims, No Drawings

PROCESS FOR THE PREPARATION OF 3'-AMINOPROPYL 2-SULFATOETHYL SULFONE

The invention relates to a process for the preparation of 3'-aminopropyl 2-sulfatoethyl sulfone in good yields by reacting in a one-pot process allylamine with mercaptoethanol in aqueous sulfuric acid at temperatures of about 50° C. to the boiling point of the reaction mixture in the presence of free-radical initiators, oxidizing the reaction mixture formed with hydrogen peroxide in the presence of catalytic amounts of transitionmetal compounds, then adding sulfuric acid and evaporating the mixture to dryness.

3'-Aminopropyl 2-sulfatoethyl sulfone is an important prerequisite for the preparation of reactive dyes (EP 0,141,776).

The preparation of 3'-aminopropyl 2-sulfatoethyl sulfone has not yet been described in the literature. However, the preparation of 2'-aminoethyl 2-sulfatoetyl sulfone is known from the literature. According to US Pat. No. 2,824,887, it is prepared by reacting 2-chloroethylamine hydrochloride with the sodium salt of mercaptoethanol and oxidizing the 2'-aminoethyl 2-hydroxyethyl sulfide hydrochloride thus obtained with peracetic acid to give 2'-aminoethyl 2-hydroxyethyl sulfone hydrochloride.

European Patent No. 0,141,776 (page 13) describes methods for sulfating 2'-aminoethyl 2-hydroxyethyl sulfone hydrochloride or similar alkyl hydroxyethyl sulfones using sulfuric acid or chlorosulfonic acid at temperatures of 10 to 80° C. If it were desired to prepare 3'-aminopropyl 2-sulfatoethyl sulfone in an analogous manner, the formation of two equivalents of sodium chloride in the preparation of 3'-aminopropyl 2-hydroxyethyl sulfide (precursor) would have to be accepted. An improved process for the preparation of this sulfide which operates without the formation of salt is described in DE 2,040,620, in which allylamine is reacted with mercaptoethanol at 50 to 150° C. with the addition of azoisobutyronitrile (AIBN). The reference cited does not give any yields for this process. Upon repeating the process (Example 4), yields of only 56.6% of theory were obtained. Thus, it can be stated that these known processes for the preparation of 2'-aminoethyl 2-sulfatoethyl sulfone and 3'-aminopropyl 2-hydroxyethyl sulfide (precursor) do not meet the requirements of an industrial process.

Accordingly, there was a need for an economical and technically feasible process for the preparation of 3'-aminopropyl 2-sulfatoethyl sulfone.

It has now been found that 3'-aminopropyl 2-sulfatoethyl sulfone can be prepared in very good yields (>95% of theory) by reacting in a one-pot process allylamine with mercaptoethanol in dilute sulfuric acid at temperatures of about 50° C. to the boiling point, preferably about 70° C. to about 100° C., in the presence of a free-radical initiator, oxidizing the resulting reaction mixture with hydrogen peroxide in the presence of catalytic amounts of a compound of a transition metal of the periodic table of the elements, preferably a compound of tungsten or vanadium, as the oxidation catalyst at temperatures of about 70 to about 100° C., preferably about 80 to about 90° C., and, after sulfuric acid has been added in such an amount that the total amount of sulfuric acid in the mixture is at least 1 mol, relative to the allylamine used, evaporating the mixture to dryness.

The detailed procedure of the process according to the invention can be as follows: it can either be such that both reactants are mixed in aqueous sulfuric acid and brought to the reaction temperature in the presence of air and/or pure oxygen, or such that allylamine is initially introduced in about 0.5 to about 0.7 mol of aqueous sulfuric acid per mole of allylamine and mercaptoethanol is metered in at temperatures of about 50° C. to the boiling point of the reaction mixture, preferably about 70 to about 100° C. It is also possible to initiate the reaction with a free-radical former from the series of azo compounds, such as, for example, azoisobutyronitrile, or of peroxide compounds, such as, for example, benzoyl peroxide. A catalytic amount of, for example, a tungsten or vanadium compound is then added to the reaction mixture thus obtained at temperatures of about 70° C. to the boiling point of the reaction mixture. About 1.9 to about 2.2 mol of hydrogen peroxide solution per mole of allylamine are then metered in at these temperatures. After the mixture has been stirred at about 70 to about 100° C. for about 1 hour, about 0.3 to about 0.7 mol of sulfuric acid, relative to 1 mol of allylamine used, is added, so that the overall sulfuric acid amount is at least 1 mol, relative to 1 mol of allylamine used, and finally the mixture is evaporated to dryness at, towards the end, about 150° C. in vacuo. 3'-Aminopropyl 2-sulfatoethyl sulfone remains as residue in high yields of >95%.

It is appropriate to react 1 mol of allylamine with about 0.9 to about 1.5 mol, preferably with about 0.95 to about 1.05 mol, of mercaptoethanol in dilute sulfuric acid which advantageously has a concentration of about 10 to about 50 percent by weight. It is also possible to use a less or more highly concentrated sulfuric acid as the reaction medium, but if a sulfuric acid concentration of <10 percent by weight is used, a poorer space-time yield has to be accepted. If more highly concentrated sulfuric acid is used, the starting compounds can no longer completely go into solution.

As for the amount used of free-radical initiator, the rule is first to use about 0.1 g per mole of allylamine used. As the reaction progresses, about 0.1 g each of further free-radical initiator per mole of allylamine used is then added about every 4 hours. Although it is possible to add larger amounts of free-radical initiator, they do not offer any further advantages in practice.

The amount of sulfuric acid added again after the oxidation is complete advantageously does not exceed 1.2 mol, relative to the allylamine used. Although it is also possible to add a larger amount of sulfuric acid, this does not result in any advantage.

The process according to the invention is usefully carried out at atmospheric pressure; however, it can also be carried out at elevated pressure The advantage of the process according to the invention is that no waste products are formed apart from the water which is distilled off. Furthermore, for the first time it is possible to carry out the reaction as a one-pot process, which renders the process very favorable from the point of view of economics and ecology. It is true that oxidation using hydrogen peroxide and esterification using sulfuric acid used in this process are known in principle, but the free-radical addition reaction of mercaptoethanol with allylamine and the combination of all three process steps to give a one-pot reaction are novel. It must be considered surprising that allylamine reacts with mercaptoethanol in aqueous sulfuric acid in the presence of air and/or oxygen in high yields, especially since German Patent No. 1,593,999 has shown that the use of oxidative free-radical initiators in the reaction of allylamine with mercaptopropionic acid leads to undesired by-products.

The examples which follow illustrate the invention in more detail without limiting it thereto.

EXAMPLE 1 (3'-aminopropyl 2-sulfatoethyl sulfone)

100.0 g of ice and 61.3 g (0.6 mol) of 96% sulfuric acid are initially introduced into a 1-l four-neck flask equipped with stirrer, dropping funnel, thermometer and reflux condenser. 57.1 g (1.0 mol) of allylamine are then run in. 0.1 g of azoisobutyronitrile (AIBN) is then added to the mixture and 78.1 g (1.0 mol) of mercaptoethanol are metered in. Stirring at 80 to 85° C. is then continued for a total of 35 hours, metering in a further 0.1 g each of AIBN at intervals of 4 hours each. After the reaction is complete, 1.0 g of sodium tungstate dihydrate is added at 80° C., and 113.3 g (1.0 mol) of 30% hydrogen peroxide are metered in over a period of 1 hour. To maintain the temperature at 80° C., the reaction mixture must be cooled with ice water. Another 113.3 g (1.0 mol) of 30% hydrogen peroxide are then metered in at 80° C. After addition is complete, stirring at 80° C. is continued for 1 hour. The hydroxyethyl sulfone is esterified by adding 46.0 g (0.45 mol) of 96% sulfuric acid. The reaction mixture is added dropwise to a laboratory kneader at a temperature of 80° C./200 mbar, and the temperature is then slowly increased to 150° C./1 mbar. It is finally evaporated to dryness to give 254.7 g of 3'-aminopropyl 2-sulfatoethyl sulfone having a purity of 93.6%, which corresponds to a yield of 96.4% of theory.

Melting point: 235–240° C. (decomposition)

$^1$H-NMR ([D$_6$]DMSO): $\delta = 2.0$ (q, J=7Hz;CH$_2$CH$_2$CH$_2$CH$_2$;2H), 2.9 (m;CH$_2$NH$_3^+$; 2H), 3.2 (m;SO$_2$CH$_2$CH$_2$;2H), 3.4 (t, J=7Hz;CH$_2$CH$_2$SO$_2$), 4.1 (t, J=7Hz;CH$_2$OSO$_3^-$;2H), 7.7 (broad; NH$_3^+$;3H). IR (KBr): 3160, 2990, 2935, 1320, 1290, 1205, 1060 cm$^{-1}$.

EXAMPLE 2 (3'-aminopropyl 2-sulfatoethyl sulfone)

200.0 g of ice and 51.1 g (0.5 mol) of 96% sulfuric acid are initially introduced into a 1-l four-neck flask equipped with stirrer, dropping funnel, thermometer and reflux condenser. 57.1 g (1.0 mol) of allylamine are then run in. 78.1 g (1.0 mol) of mercaptoethanol are then metered in. Stirring at 100° C is then continued for a total of 40 hours and air is passed through the reaction mixture at the same time. After the reaction is complete, 0.5 g of sodium tungstate dihydrate is added at 80° C., and 113.3 g (1.0 mol) of 30% hydrogen peroxide are metered in over a period of 1 hour. To maintain the temperature at 80° C., the mixture must be cooled with ice water. Another 113.3 g (1.0 mol) of 30% hydrogen peroxide are then metered in at 80° C. After addition is complete, stirring at 80° C is continued for 1 hour. The hydroxyethyl sulfone is esterified by adding 56.3 g (0.55 mol) of 96% sulfuric acid. The reaction mixture is added dropwise to a laboratory kneader at a temperature of 80° C./200 mbar, and the temperature is then slowly increased to 150° C./1 mbar. The mixture is finally evaporated to dryness to give 249.5 g of 3'-aminopropyl 2-sulfatoethyl sulfone having a purity of 96.5%, which corresponds to a yield of 97.3% of theory.

Melting point: 235–240° C. (decomposition)

The spectroscopic data are identical to those given at the end of Example 1.

EXAMPLE 3 (3'-aminopropyl 2-sulfatoethyl sulfone)

100.0 g of ice and 56.3 g (0.55 mol) of 96% sulfuric acid are initially introduced into a 1-l four-neck flask equipped with stirrer, dropping funnel, thermometer and reflux condenser. 57.1 g (1.0 mol) of allylamine and 78.1 g (1.0 mol) of mercaptoethanol are then added. 0.1 g of dibenzoyl peroxide is added to the reaction mixture obtained and stirring is continued at 80 to 85° C. for a total of 45 hours, adding 0.1 g each of benzoyl peroxide after a period of 5 hours each. After reaction is complete, 1.0 g of sodium tungstate dihydrate is added at 80° C. 226.6 g (1.0 mol) of 30% hydrogen peroxide are then metered in over a period of 2 hours. After addition is complete, stirring at 80° C. is continued for 1 hour. The hydroxyethyl sulfone is esterified by adding 56.3 g (0.55 mol) of 96% sulfuric acid. The reaction mixture is added dropwise to a laboratory kneader at a temperature of 80° C./200 mbar, and the temperature is then slowly increased to 150° C./1 mbar. It is finally evaporated to dryness by distillation to give 256.5 g of 3'-aminopropyl 2-sulfatoethyl sulfone having a purity of 91.8%, which corresponds to a yield of 94.6% of theory.

Melting point: 235–240° C. (decomposition)

The spectroscopic data are identical to those given at the end of Example 1.

The procedure as given above is repeated, replacing the sodium tungstate dihydrate by the same amount of sodium metavanadate (NaVO$_3$), to give the same result.

EXAMPLE 4 (3'-aminopropyl 2-hydroxyethyl sulfide)

Comparative example according to the procedure of Example 3, page 18, of DE 2,040,620

57.0 g (1.0 mol) of allylamine are added dropwise at 80 to 90° C. over a period of 2 hours to 78.1 g (1.0 mol) of mercaptoethanol to which 0.5 g of AIBN has been added. Stirring at 80 to 90° C. is then continued for 10 hours to give 126.8 g of 3'-aminopropyl 2-hydroxyethyl sulfide having a purity of 60.4%, which corresponds to a yield of 56.6% of theory.

What is claimed is:

1. A process for the preparation of 3'-aminopropyl 2-sulfatoethyl sulfone, which comprises reacting in a one-pot process allylamine with mercaptoethanol in dilute sulfuric acid at a temperature of about 50° C. to the boiling point in the presence of a free-radical initiator, oxidizing the resulting reaction mixture with hydrogen peroxide in the presence of catalytic amount of a tungsten or vanadium compound as the oxidation catalyst at a temperature of about 70 to about 100° C., and, after sulfuric acid has been added in such an amount that the total amount of sulfuric acid in the mixture is at least 1 mol, relative to the allylamine used, evaporating the mixture to dryness.

2. The process as claimed in claim 1, wherein the allylamine is reacted with the mercaptoethanol in the aqueous sulfuric acid at temperatures of about 70 to about 100° C.

3. The process as claimed in claim 1, wherein the reaction is carried out in the presence of pure oxygen as the free-radical initiator.

4. The process as claimed in claim 2, wherein the reaction is carried out in the presence of a mixture of oxygen and an inert gas as the free-radical initiator.

5. The process as claimed in claim 1, wherein the reaction is carried out in the presence of air as the free-radical initiator.

6. The process as claimed in claim 1, wherein the reaction is carried out in the presence of an azo compound as the free-radical initiator.

7. The process as claimed in claim 1, wherein the reaction is carried out in the presence of azoisobutyronitrile as the free-radical initiator.

8. The process as claimed in claim 1, wherein the reaction is carried out in the presence of a peroxide compound as the free-radical initiator.

9. The process as claimed in claim 1, wherein the reaction is carried out in the presence of benzoyl peroxide as the free-radical initiator.

10. The process as claimed in claim 1, wherein the oxidation is carried out in the presence of $Na_2WO_4 \cdot 2H_2O$ as the oxidation catalyst.

11. The process as claimed in claim 1, wherein the oxidation is carried out in the presence of $NaVO_3$ as the oxidation catalyst.

12. The process as claimed in claim 1, wherein the reaction is carried out at atmospheric pressure or superatmospheric pressure.

* * * * *